US008097042B2

(12) United States Patent
Slemker et al.

(10) Patent No.: US 8,097,042 B2
(45) Date of Patent: Jan. 17, 2012

(54) DOUBLE-WALL PROSTHETIC LIMB ASSEMBLY

(75) Inventors: Tracy C. Slemker, Clayton, OH (US);
Steven Steinbarger, Clayton, OH (US);
Robert Hoskins, Clayton, OH (US)

(73) Assignee: Prosthetic Design, Inc., Clayton, OH (US)

( * ) Notice: Subject to any disclaimer, the term of this patent is extended or adjusted under 35 U.S.C. 154(b) by 579 days.

(21) Appl. No.: 11/650,304

(22) Filed: Jan. 5, 2007

(65) Prior Publication Data

US 2007/0168045 A1 Jul. 19, 2007

Related U.S. Application Data

(60) Provisional application No. 60/756,430, filed on Jan. 5, 2006.

(51) Int. Cl.
*A61F 2/80* (2006.01)
*A61F 2/78* (2006.01)
(52) U.S. Cl. ............... 623/34; 623/33; 623/36; 623/38
(58) Field of Classification Search .............. 623/33, 623/34, 32, 35–38
See application file for complete search history.

(56) References Cited

U.S. PATENT DOCUMENTS

| 5,226,918 | A | * | 7/1993 | Silagy et al. | ............ 623/32 |
| 5,263,990 | A | * | 11/1993 | Handal | ............ 623/57 |
| 5,662,715 | A |   | 9/1997 | Slemker |  |
| 5,702,489 | A | * | 12/1997 | Slemker | ............ 623/34 |
| 5,728,166 | A | * | 3/1998 | Slemker | ............ 623/36 |
| 5,824,111 | A |   | 10/1998 | Schall et al. |  |
| 5,885,509 | A | * | 3/1999 | Kristinsson | ............ 264/314 |
| 5,888,217 | A | * | 3/1999 | Slemker | ............ 623/36 |
| 5,888,234 | A | * | 3/1999 | Littig | ............ 623/38 |

(Continued)

FOREIGN PATENT DOCUMENTS

WO WO 00/03665 A1 * 1/2000

OTHER PUBLICATIONS

Compact Oxford English Dictionary, 2009, Oxford University Press, online version from www.askoxford.com.*

(Continued)

*Primary Examiner* — David Isabella
*Assistant Examiner* — Marcia Hoffman
(74) *Attorney, Agent, or Firm* — Baker & Hostetler LLP (57) ABSTRACT

In one embodiment, a double-wall prosthetic limb socket assembly includes: (a) a first substantially rigid inner-wall socket adapted to receive a patient's residual limb; and (b) a second substantially rigid outer-wall socket seating the first inner-wall socket therein, the second outer-wall socket including, (i) a distal, circular base-plate; and (ii) a molded circumferential wall bonded to and extending proximally from the distal, circular base-plate; where the circular base-plate includes a vacuum port extending radially from a circumferential outer side of the base-plate in fluid communication with a vacuum channel extending through the circular base-plate and out through an outlet hole in a proximal side of the circular base-plate; such that when the vacuum port is coupled to a vacuum pump, the vacuum will help to draw the first inner-wall socket into the second outer-wall socket. A resilient, roll-on liner with a substantially closed distal end and an open proximal end interposes the substantially rigid inner and outer wall sockets.

18 Claims, 9 Drawing Sheets

U.S. PATENT DOCUMENTS

| | | | |
|---|---|---|---|
| 5,904,722 A * | 5/1999 | Caspers | 623/34 |
| 5,928,290 A * | 7/1999 | Gramnas | 623/33 |
| 6,033,440 A | 3/2000 | Schall et al. | |
| 6,063,125 A * | 5/2000 | Arbogast et al. | 623/34 |
| 6,106,559 A * | 8/2000 | Meyer | 623/33 |
| 6,267,787 B1 * | 7/2001 | Capper et al. | 623/36 |
| 6,287,345 B1 * | 9/2001 | Slemker et al. | 623/34 |
| 6,358,453 B1 * | 3/2002 | Slemker et al. | 264/222 |
| 6,361,569 B1 | 3/2002 | Slemker et al. | |
| 6,416,703 B1 * | 7/2002 | Kristinsson et al. | 264/257 |
| 6,440,172 B1 * | 8/2002 | Davant et al. | 623/36 |
| 6,440,173 B1 * | 8/2002 | Meyer | 623/36 |
| 6,458,163 B1 * | 10/2002 | Slemker et al. | 623/38 |
| 6,511,513 B1 * | 1/2003 | Laghi | 623/33 |
| 6,554,868 B1 * | 4/2003 | Caspers | 623/34 |
| 6,572,656 B1 * | 6/2003 | Laghi | 623/33 |
| 6,572,657 B2 * | 6/2003 | Laghi | 623/33 |
| 6,576,020 B2 * | 6/2003 | Laghi | 623/33 |
| 6,576,021 B2 * | 6/2003 | Laghi | 623/33 |
| 6,579,323 B2 * | 6/2003 | Laghi | 623/33 |
| 6,589,288 B2 * | 7/2003 | McDowell et al. | 623/33 |
| 6,596,027 B2 * | 7/2003 | Laghi | 623/33 |
| 6,596,028 B1 * | 7/2003 | Laghi | 623/33 |
| 6,605,118 B2 * | 8/2003 | Capper et al. | 623/36 |
| 6,626,951 B1 * | 9/2003 | Gramnas | 623/33 |
| 6,669,736 B2 * | 12/2003 | Slemker et al. | 623/32 |
| 6,689,171 B2 * | 2/2004 | Slemker et al. | 623/33 |
| 6,761,742 B2 | 7/2004 | Caspers | |
| 6,926,742 B2 | 8/2005 | Caspers et al. | |
| 2002/0042659 A1 * | 4/2002 | Ingimarsson | 623/33 |
| 2002/0091449 A1 * | 7/2002 | Caspers et al. | 623/34 |
| 2002/0103544 A1 * | 8/2002 | McDowell et al. | 623/33 |
| 2003/0195636 A1 * | 10/2003 | Coop | 623/36 |
| 2005/0131549 A1 * | 6/2005 | Caspers | 623/34 |
| 2007/0055383 A1 * | 3/2007 | King | 623/34 |

OTHER PUBLICATIONS

Merriam-Webster Online Dictionary, Definition "Liner", Accessed Jan. 11, 2010.*

* cited by examiner

FIG. 1

PRIOR ART

FIG. 2

PRIOR ART

DOUBLE-WALL PROSTHETIC LIMB ASSEMBLY

CROSS REFERENCE TO RELATED APPLICATIONS

The present application claims the benefit from U.S. Provisional App. Ser. No. 60/756,430, filed Jan. 5, 2006, the entire disclosure of which is incorporated herein by reference.

BACKGROUND

Figure 1:
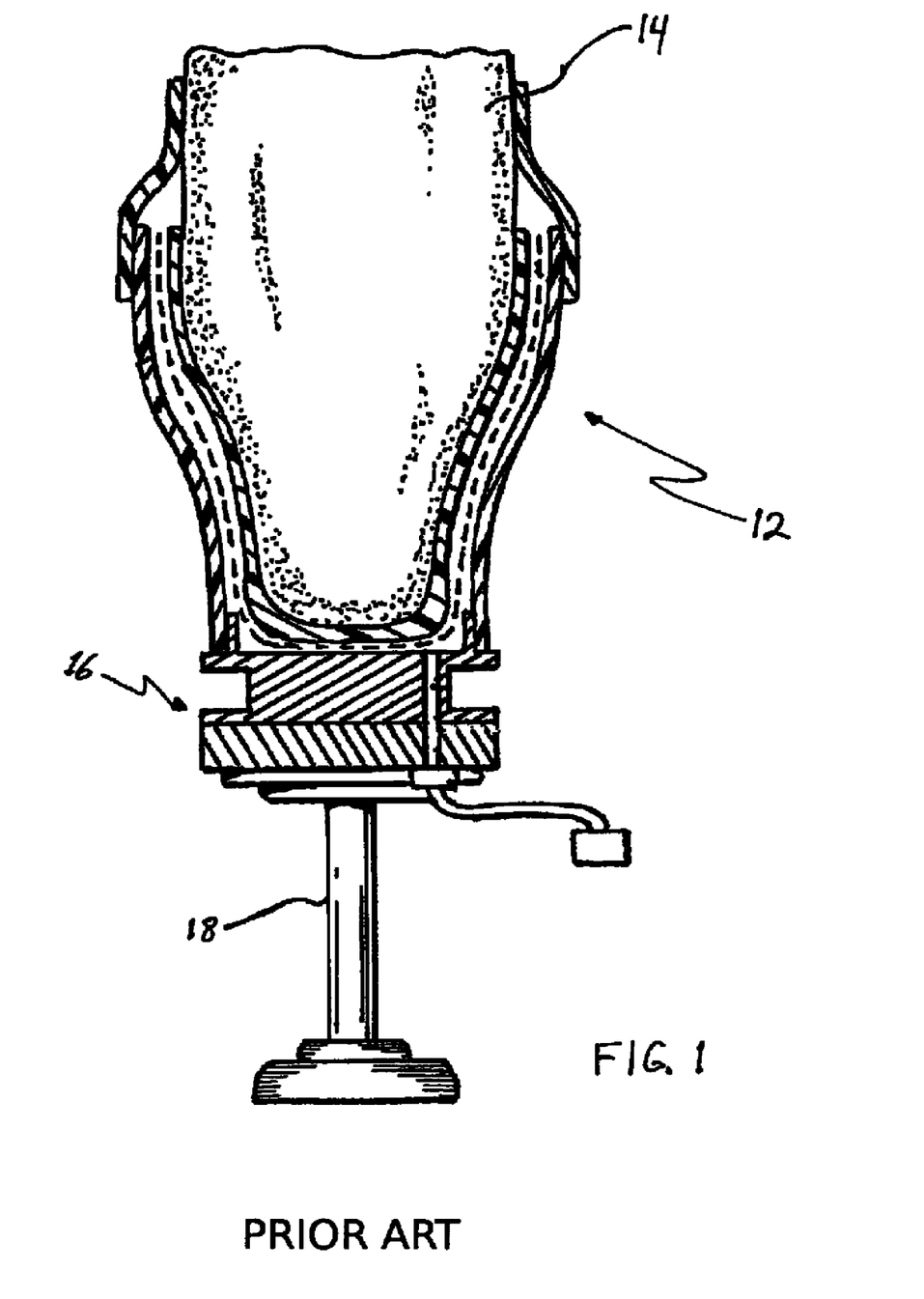
FIGS. 1 and 2 show two embodiments of a Vacuum Assisted Socket System (VASS) socket and attachment plate joined to a prosthetic limb, according to the prior art.
Figure 2:
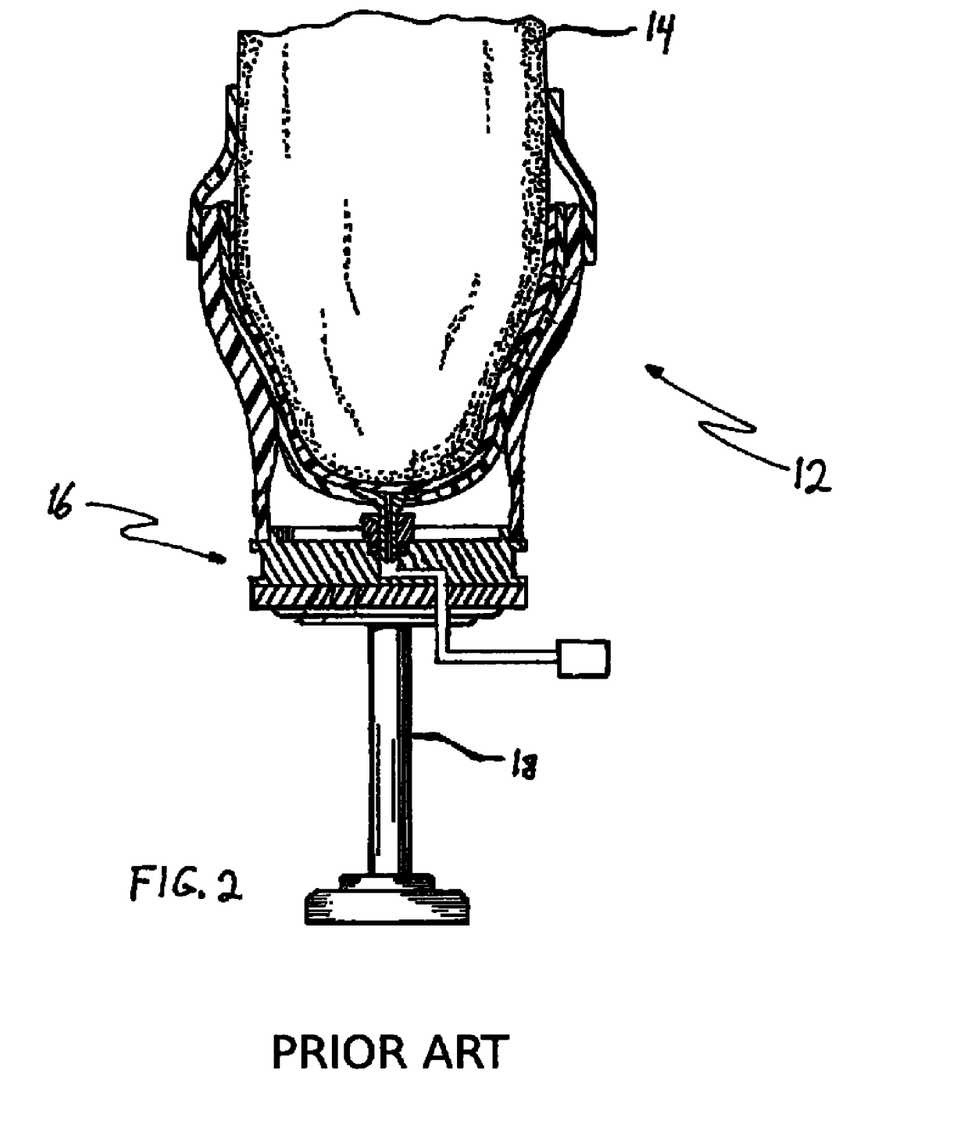

When attaching a prosthetic limb to an amputee's residual limb, a thermoplastic socket having a cavity shaped to receive the residual limb is typically fitted over the residual limb, and the prosthetic limb is typically joined to the bottom of the socket using an attachment plate. The socket can be held in place on the residual limb using the Vacuum Assisted Socket System (VASS)™, developed by Otto-Bock HealthCare LP and described in U.S. Pat. Nos. 6,761,742 and 6,926,742, the disclosures of which are incorporated herein by reference. FIGS. 1 and 2 show two embodiments of a Vacuum Assisted Socket System (VASS) socket and attachment plate joined to a prosthetic limb, according to the prior art. The socket 12 fits over the patient's residual limb 14 and is held in place by a vacuum seal formed by evacuating air from the space between the socket 12 and the residual limb 14. The socket features an attachment plate 16 on its bottom end for joining the socket to the hardware of the prosthetic limb 18. The structure and function of the Vacuum Assisted Socket System (VASS) depicted in FIGS. 1 and 2 are described in U.S. Pat. No. 6,926,742.

In a dual socket system (double wall socket system), an inner socket is fitted to the patient's limb, while the pylon assembly is attached to an outer socket. The outer socket slides over the inner socket. The two sockets are typically held to each other by some mechanical means, such as a latch. The inner socket is fabricated to fit precisely around the patient's residual limb. It is held to the patients residual limb by some mechanical means, such as a vacuum. The outer socket is formed to accept the inner socket and any additional components associated therewith in proper alignment and then laminating the outer socket over the mold. The outer socket has traditionally been formed by fabricating a temporary mold on the distal end of the inner socket to create the proper spacing and alignment. This process is labor intensive, can be imprecise, and often requires fabrication at a central location in a specialized facility.

There is a need for a standardized method that saves labor, helps to ensure appropriate alignment, and allows for fabrication at decentralized locations.

SUMMARY

The present invention relates to a double wall prosthetic limb assembly, a vacuum attachment plate component of the outer-wall socket and a method for fabricating double wall prosthetic limb assemblies. The method involves the use of a prefabricated tooling system for fabricating a dual socket for a prosthetic limb.

It is a first aspect of the present invention to provide a double-wall prosthetic limb socket assembly that includes: (a) a first inner-wall socket adapted to receive a patient's residual limb; and (b) a second outer-wall socket seating the first inner-wall socket therein, the second outer-wall socket including, (i) a distal, circular base-plate; and (ii) a molded circumferential wall bonded to and extending proximally from the distal, circular base-plate; where the circular base-plate includes a vacuum port extending radially from a circumferential outer side of the base-plate in fluid communication with a vacuum channel extending through the circular base-plate and out through an outlet hole in a proximal side of the circular base-plate; such that when the vacuum port is coupled to a vacuum pump, the vacuum will help to draw the first inner-wall socket into the second outer-wall socket. In a more detailed embodiment, the circular base-plate includes one or more indentations extending into a circumferential outer side of the circular base-plate into which material of the molded circumferential wall is received, thus facilitating a mechanical bond between the circular base-plate and the molded circumferential wall. In a further detailed embodiment, the molded circumferential wall includes layers of fabric-type material impregnated with cured resin. In yet a further detailed embodiment, the circular base-plate is less than 0.75 inches thick.

In an alternate detailed embodiment of the first aspect of the present invention, the assembly further includes: (c) a first one of a female and a male component of a mechanical lock seated between the first inner-wall socket and the second outer-wall socket over a proximal end of the circular base-plate; and (d) a complimentary component of the first component of the mechanical lock extending from the first inner-wall socket and mating with the first component of the mechanical lock thus providing a mechanical lock between the first inner-wall socket and second outer-wall socket. In a further detailed embodiment, the first component of the mechanical lock is a male, ratchet-type interlock pin and the complimentary component of the mechanical lock is a female, biased-pawl type lock base. In yet a further detailed embodiment, the interlock pin extends from a resilient sleeve covering the first inner-wall socket and includes a vacuum channel extending completely therethrough in fluid communication with the outlet hole of the circular base-plate when locked into the lock base and providing a vacuum the resilient sleeve and the inner-wall socket.

In another alternate detailed embodiment of the first aspect of the present invention the distal end of the circular base-plate includes a fastener for coupling to a prosthetic limb upright assembly.

In another alternate detailed embodiment of the first aspect of the present invention the distal end of the circular base is coupled to a prosthetic limb pyramid coupling component.

It is a second aspect of the present invention to provide a double-wall prosthetic limb socket assembly that includes: (a) a first inner-wall socket adapted to receive a patient's residual limb; (b) a second outer-wall socket seating the first inner-wall socket therein, the second outer-wall socket including, (i) a distal, circular base-plate, and (ii) a molded circumferential wall bonded to and extending proximally from the distal, circular base-plate; (c) a first one of a female and a male component of a mechanical lock seated between the first inner-wall socket and the second outer-wall socket over a proximal end of the circular base-plate; and (d) a complimentary component of the first component of the mechanical lock extending from the first inner-wall socket and mating with the first component of the mechanical lock thus providing a mechanical lock between the first inner-wall socket and second outer-wall socket; where the circular base-plate including a vacuum port extending an outer surface of the base-plate in fluid communication with a vacuum channel extending through the circular base-plate and out through an outlet hole in a proximal side of the circular base-plate; thereby, when the vacuum port is coupled to a vacuum pump, the vacuum will help to draw the first inner-wall socket into the second outer-wall socket. In a more detailed embodiment, the first component of the mechanical lock is a male, ratchet-type interlock pin and the complimentary component of the mechanical lock is a female, biased-pawl type lock base. In a further detailed embodiment, the interlock pin extends from a resilient sleeve covering the first inner-wall socket and includes a vacuum channel extending completely therethrough in fluid communication with the outlet hole of the circular base-plate when locked into the lock base and providing a vacuum the resilient sleeve and the inner-wall socket.

In an alternate detailed embodiment of the second aspect of the present invention the distal end of the circular base-plate includes a fastener for coupling to a prosthetic limb upright assembly.

In another alternate detailed embodiment of the second aspect of the present invention the distal end of the circular base is coupled to a prosthetic limb pyramid coupling component.

It is a third aspect of the present invention to provide a double-wall prosthetic limb socket assembly that includes (a) a first inner-wall socket adapted to receive a patient's residual limb; and (b) a second outer-wall socket seating the first inner-wall socket therein, the second outer-wall socket including, (i) a distal, circular base-plate and (ii) a molded circumferential wall bonded to and extending proximally from the distal, circular base-plate; where the circular base-plate including one or more indentations extending into a circumferential outer side of the circular base-plate into which material of the molded circumferential wall is received, thus facilitating a mechanical bond between the circular base-plate and the molded circumferential wall; and where the circular base-plate also includes a vacuum port extending an outer surface of the base-plate in fluid communication with a vacuum channel extending through the circular base-plate and out through an outlet hole in a proximal side of the circular base-plate; thereby, when the vacuum port is coupled to a vacuum pump, the vacuum will help to draw the first inner-wall socket into the second outer-wall socket. In a more detailed embodiment, the molded circumferential wall includes layers of fabric-type material impregnated with cured resin. In a further detailed embodiment, the circular base-plate is less than 0.75 inches thick.

It is a fourth aspect of the present invention to provide a method for fabricating a double-wall prosthetic limb socket assembly comprising the steps of: (a) fabricating a first inner-wall socket that is adapted to receive a patient's residual limb; (b) installing a positive mold end-block over a distal end of the first inner-wall socket, the positive mold end-block having outer dimensions approximating outer dimensions of components to be installed between the distal end of the inner-wall socket and an outer-wall socket; (c) installing a distal-end attachment plate component of the outer-wall socket over a distal end of the positive mold end-block, the distal-end attachment plate component having one or more indentations extending into a circumferential outer side of the distal-end attachment plate into which material of a molded circumferential wall of the second outer-wall socket will be received; and (d) molding the circumferential wall of the second outer-wall socket over the first inner-wall socket, over lateral sides of the positive mold end-block and into the one or more indentations extending into the circumferential outer side of the distal end attachment plate. In a further detailed embodiment, the method further includes the step of (e) after the circumferential wall of the second outer-wall socket has sufficiently solidified, replacing the positive mold end-block with the components to be installed between the distal end of the inner-wall socket and an outer-wall socket.

In an alternate detailed embodiment of the fourth aspect of the present invention, the distal-end attachment plate includes a vacuum port extending an outer surface of the base-plate in fluid communication with a vacuum channel extending through the distal-end attachment plate and out through an outlet hole in a proximal side of the circular base-plate, and the method includes, prior to the molding step, a step of covering the vacuum port to keep the vacuum port from being contacted by material of the molded circumferential wall of the second outer-wall socket during the molding step. In a further detailed embodiment, the vacuum port extends radially from a lateral outer side of the distal-end attachment plate. In yet a further detailed embodiment, the distal-end attachment plate is substantially disc-shaped and 0.75 inches thick or less.

In another alternate detailed embodiment of the fourth aspect of the present invention components installed between the distal end of the inner-wall socket and an outer-wall socket include an actuator mechanism extending-radially outward beyond the circumferential wall of the outer-wall socket; the positive mold end-block includes a lateral projection extending therefrom that has outer dimensions approximating outer dimensions of a hole in the circumferential wall of the outer-wall socket needed to facilitate passage of the actuator mechanism extending therethrough; and the molding step molds the circumferential wall of the second outer-wall socket over at least portions of the lateral projection.

In another alternate detailed embodiment of the fourth aspect of the present invention the first inner-wall socket includes a distal end-component with a threaded hole extending out from a distal end surface o the distal end-component; and the step of installing the positive mold end-block over the distal end of the first inner-wall socket includes a step of threading a threaded fastener extending from the positive mold end-block into the threaded hole of the distal end-component. In a more detailed embodiment, the method further includes the step of, after the circumferential wall of the second outer-wall socket has sufficiently solidified, (e) replacing the positive mold end-block with the components to be installed between the distal end of the inner-wall socket and an outer-wall socket, and replacing the threaded fastener with a coupling component to extend from the distal end-component of the inner-wall socket and to mate with an associated component installed between the distal end of the inner-wall socket. In a further detailed embodiment, the components installed between the distal end of the inner-wall socket include a shuttle lock component; and the coupling component extending from the distal end-component of the inner-wall socket includes an interlock pin for selectively engaging with the shuttle lock component.

In another alternate detailed embodiment of the fourth aspect of the present invention the molding step includes the step of applying one or more layers of resin-soaked fabric-like material over the first inner-wall socket and over lateral sides of the positive mold end-block and allowing the resin to at least partially cure.

DETAILED DESCRIPTION

Figure 3:
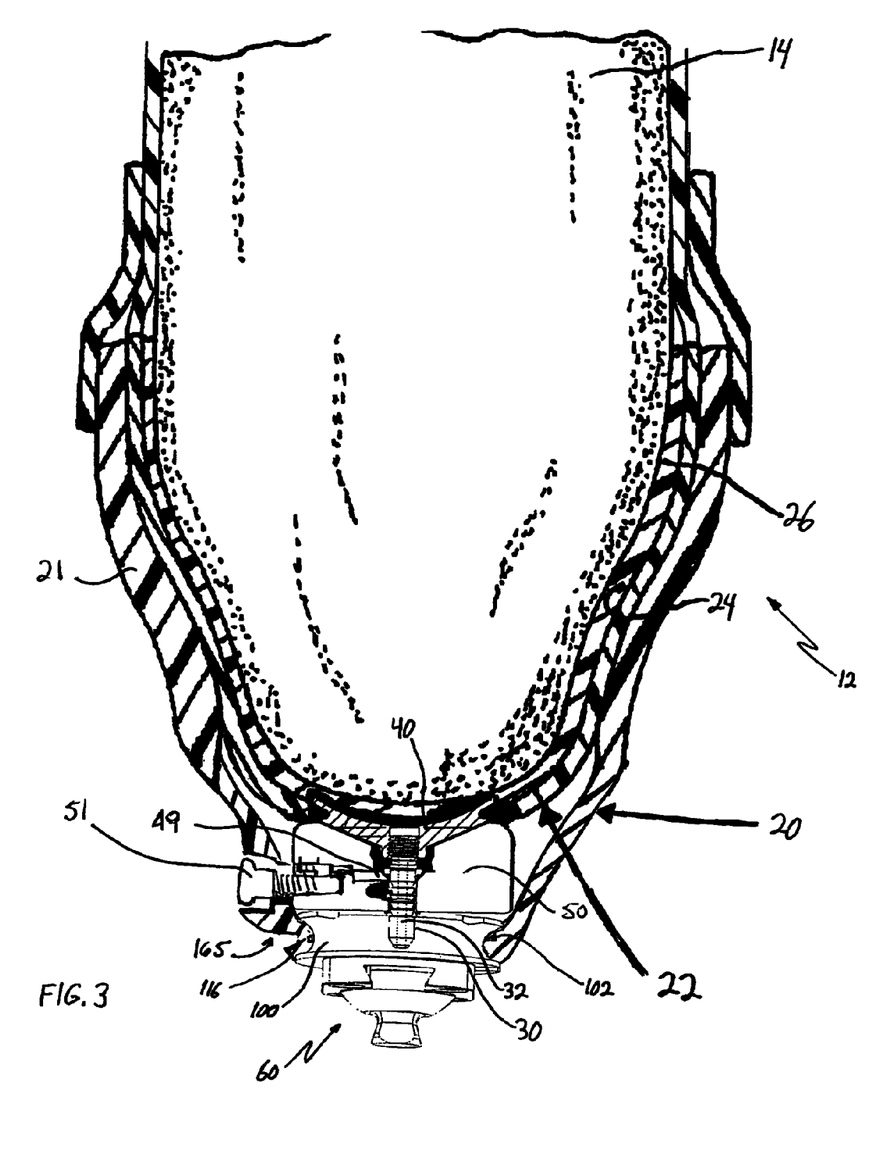
FIG. 3 shows a socket and attachment plate according to an exemplary embodiment of the present invention.

FIG. 3 shows a double-wall prosthetic limb socket assembly and associated vacuum-port attachment plate 100 according to an exemplary embodiment of the present invention. The outer socket 20 is generally conical in shape and has a circumferential wall 21 that can be made of a relatively rigid thermoplastic material or other material using techniques known to persons skilled in the art. In the exemplary embodiment, the circumferential wall 21 of the outer socket 20 is made from lamination techniques as known to those of ordinary skill in the art (producing at least one layer of fabric-like material impregnated with cured resin). The circumferential wall 21 of the outer-wall socket 20 is joined (mechanically bonded to) to a relatively thin, disc-shaped attachment plate 100. At least one circumferential indentation 102 around the edge of the attachment plate 100 facilitates the fabrication of the outer socket 20 such that the narrow (distal) end of the circumferential wall 21 is mechanically joined to the attachment plate 100 during the lamination step as described below (several smaller indentations circumferentially distributed thereover will function adequately as well; likewise, a plurality of projections circumferentially distributed thereabout will also provide a mechanical bonding function).

As seen in FIG. 3, an inner-wall socket 26, which can also be made of a relatively rigid thermoplastic material or other material using techniques known to persons skilled in the art (including lamination techniques of the exemplary embodiment), defines a cavity that receives the residual limb 14. A resilient roll-on liner 22, which can be a silicone sleeve or other similar material, can be fitted over the inner socket 26. At the bottom of the liner 22, a plate 40 is joined or molded to the liner 22. The plate 40 is relatively thin (preferably approximating the thickness of the liner 22) and generally semi-spherical or conical and includes a threaded cavity at its downward facing apex for seating a correspondingly threaded, ratchet-type interlock pin 30, otherwise known in the art as a "plunger" pin. It is also within the scope of the invention that the plate 40 be molded into the distal end of the inner socket 26' (see FIG. 9, for example), rather than the liner 22 (and that the liner 22, if used, have a distal hole for allowing at least the plunger pin, and usually some of the inner socket, to extend through).

Figure 4:
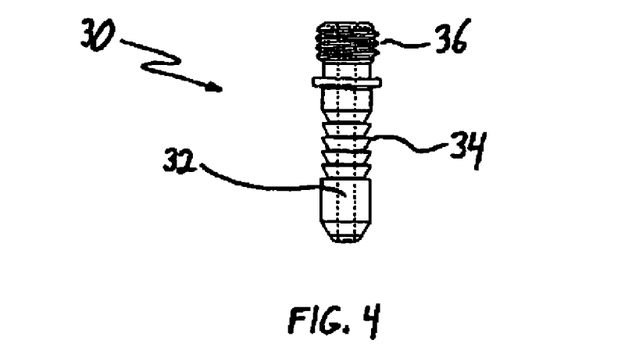
FIG. 4 shows an interlock pin for securing the inner socket and liner inside the outer socket, according to an exemplary embodiment of the present invention.
Figure 5:
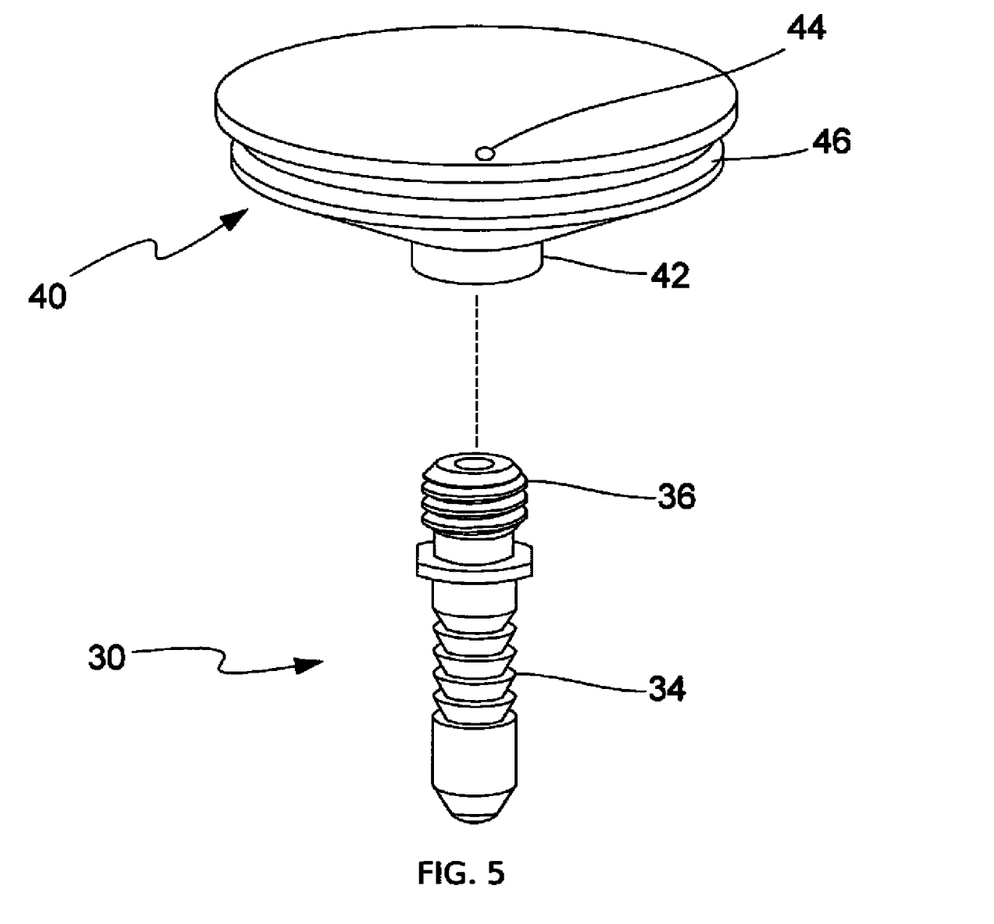
FIG. 5 shows the interlock pin and the plate that joins it to the inner socket, according to an exemplary embodiment of the present invention.

The interlock pin 30 is shown more clearly in FIGS. 4 and 5 and includes a central bore 32 extending axially along the entire length of the pin and also includes a plurality of annular barbs 34 axially distributed therealong for ratcheted engagement with a biased pawl 49 of a standard shuttle-lock mechanism 50 (for more detailed information on shuttle locks, plunger pins, and roll-on sleeves, see U.S. Pat. No. 6,361,569, the disclosure of which is incorporated by reference), see FIG. 3. It will be appreciated by those of ordinary skill that other mechanical locks can be utilized instead of the standard shuttle-lock mechanism 50 and associated interlock pin 30 described above—all of which may fall within the scope of the invention as claimed. The plate 40, which is shown more clearly in FIG. 5, includes an attachment hub 42 having a threaded interior into which the threaded portion 36 of the pin 30 may be attached. FIG. 5 also shows a circumferential groove 46 on the plate 40 to facilitate its mechanical attachment to the liner 22 during fabrication of the liner 22 (or mechanical attachment to the inner socket 26' of FIG. 9). The interior of the plate's attachment hub 42 provides an open path to a hole 44 on the upper surface of the plate. This hole 44 and the central bore 32 of the pin allow the vacuum to be applied to the space or region 24 between the liner 22 and the inner socket 26. The vacuum can be applied to the pin's central bore 32 by a pump mechanism coupled to the attachment plate 100, which is shown more clearly in FIG. 6. In the alternate embodiment of the inner socket 26' (see FIG. 9, for example) the applied vacuum could be used to hold the patient's residual limb within the inner socket 26'.

Figure 6:
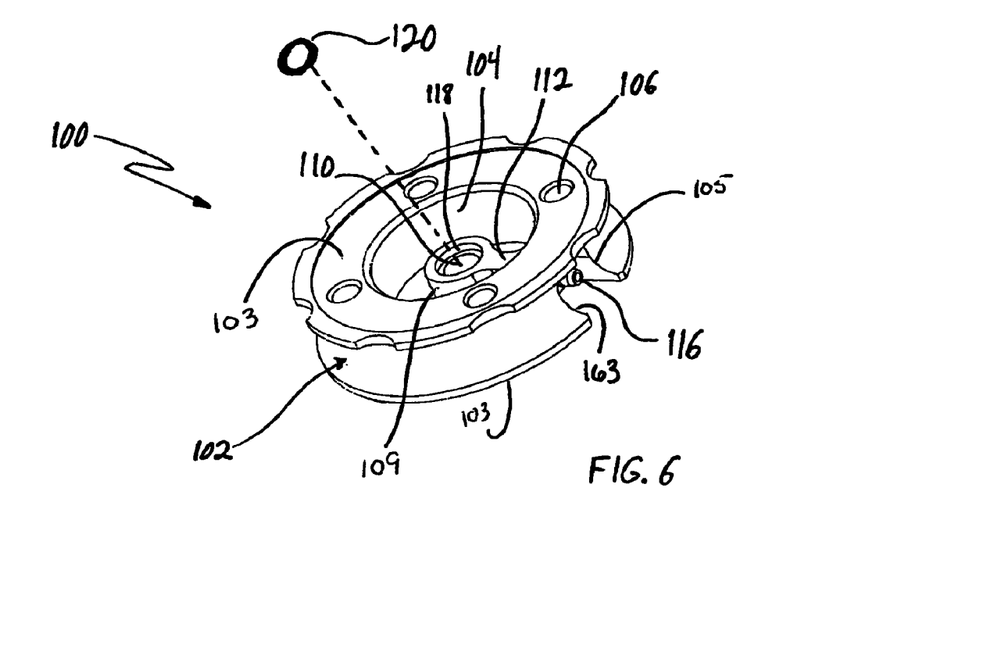
FIGS. 6 and 7 show the attachment plate according to an exemplary embodiment of the present invention.
Figure 7:
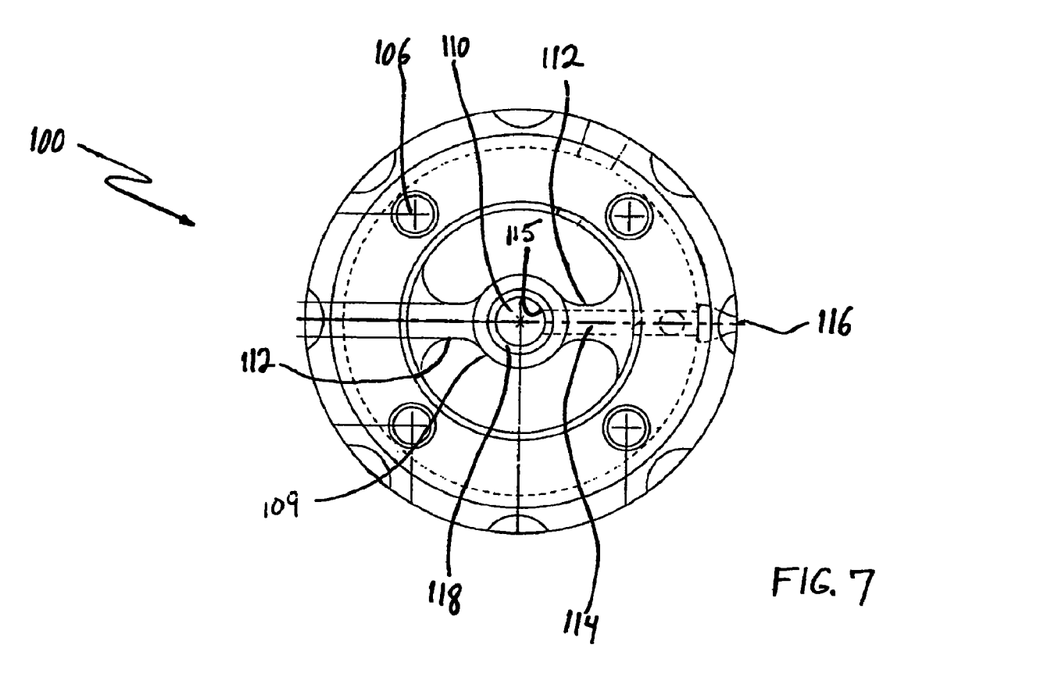

As seen in FIGS. 6 and 7, the circular attachment plate 100 has a generally annular shape, with washer-shaped upper and lower surfaces 103 being joined by an inner annular side-wall 104 and an outer annular side-wall 105 forming a circumferential indentation 102 around the perimeter of the attachment plate 100 to permit the attachment plate 100 to be fastened to the outer socket 20, as noted above. The upper and lower surfaces 103 of the attachment plate 100 are substantially parallel and are separated by a distance of approximately 0.645 inches in the exemplary embodiment. The upper and lower surfaces 103 include holes 106 into which bolts or screws can be inserted, allowing the attachment plate 100 to be joined to the shuttle lock mechanism 50 above and the prosthetic limb attachment point 60 below. The prosthetic limb attachment point 60 can be an adjustable pyramid plate, such as that described in U.S. Pat. No. 6,033,440, the disclosure of which is incorporated herein by reference, or it can be other coupling components (pyramids, pyramid-receivers, tube-clamps and the like, for example and without limitation) known to persons skilled in the art. The attachment plate 100 of the present invention has a slimmer profile than prior art attachment plates used with vacuum sockets (less than 0.75 inches in an exemplary embodiment). In an exemplary embodiment, the attachment plate 100 and shuttle lock mechanism 50, stacked together as shown in FIG. 3, have a height of 1.2 inches, which could be reduced to 0.98 inches with the current design. The holes 106 by which the attachment plate 100 of the present invention is joined to the prosthetic limb attachment point 60 are through holes rather than tapered holes, as seen on prior art attachment plates. The through holes are less susceptible to stripping than tapered holes, which is advantageous where the attachment plate is laminated to the socket, Referring again to FIGS. 6 and 7, At the center of the attachment plate 100, a hub 109 provides a receptacle 110 for receiving the interlock pin 30. This central hub 109 is fixed to the attachment plate's inner wall 104 by one or more radial bridges 112. One radial bridge contains a central bore (a vacuum channel) 114 that connects an outlet hole 115 in the hub's receptacle 110 to the vacuum port 116 for coupling to a vacuum source of a vacuum pump (not shown). An annular recess 118 at the rim of the receptacle 110 provides an annular seat for an O-ring seal 120 that can form an airtight seal with the interlock pin 30. The vacuum port 116 advantageously extends radially from the side of the attachment plate, which allows more freedom to couple various coupling components 60 and other mechanisms to the distal (bottom) surface of the attachment plate, as compared to the prior art plate shown in FIGS. 1 and 2, because the vacuum port 116 and associated vacuum pump components will not interfere with such distal coupling components. In an exemplary embodiment (as shown in FIG. 3), the vacuum port 116 is located on the same side of the attachment plate 100 as the push button 51 for the shuttle lock 50, so that the push button 51 provides additional protection for the vacuum port to decrease the chance that a patient fall or other rough handling will break the vacuum seal.

Returning to FIGS. 4 and 5, the interlock pin 30 features one or more circumferential barbs 34 around its lateral surface. These barbs allow the interlock pin 30 to be mechanically locked in place by the shuttle lock mechanism 50. The biased pawl 49 mounted within the shuttle lock mechanism 50, which can be seen in FIGS. 3 with the interlock pin 30 inserted, can engage one of the barbs 34 on the interlock pin 30, preventing the interlock pin 30 from being withdrawn from the shuttle lock mechanism 50 until the user manually releases the shuttle lock by activating the push-button 51. This shuttle lock and plunger pin engagement provides a secondary locking mechanism to hold the inner socket 26 and residual limb 14, which are contained within the liner 22, in place within the outer socket 20.

In operation, the patient's residual limb, which is dressed with the inner socket 26 and liner 22 with its interlocking pin 30, is inserted into the outer socket 20. The interlocking pin 30 first passes through the shuttle lock mechanism 50, after which it enters the receptacle 110 on the attachment plate 100. As the pin 30 enters the receptacle 110, the O-ring seal 120 forms an airtight seal between the pin 30 and the receptacle 110. A vacuum is applied, as described in U.S. Pat. No. 6,926,742, by a vacuum pump (not shown) connected to the vacuum port 116 on the attachment plate 100. The vacuum, which is applied via the vacuum port 116, the central bore 114 in the attachment plate's radial bridge 112, the central bore 32 in the pin 30, and the hole 44 in the plate 40, lowers the pressure in the region in the cavity 24 within the liner 22, within which the inner socket 22 and the patient's residual limb reside. This negative pressure applied to the residual limb greatly reduces fluid volume loss in the residual limb, as is understood by persons skilled in the art and explained in U.S. Pat. No. 6,926,742. The barb 34 on the interlocking pin 30 is engaged by the shuttle lock mechanism 50, holding the inner socket 22 containing the residual limb in place within the outer socket 20.

We now describe a method for fabricating a dual socket for a prosthetic limb using a prefabricated tooling system to create the appropriate voids and proper alignment of the outer socket relative to the inner socket and other components associated therewith. The system allows for more consistency in fabrication; eliminates the labor required to fabricate the molding traditionally used to create voids and properly align the components.

Figure 11:
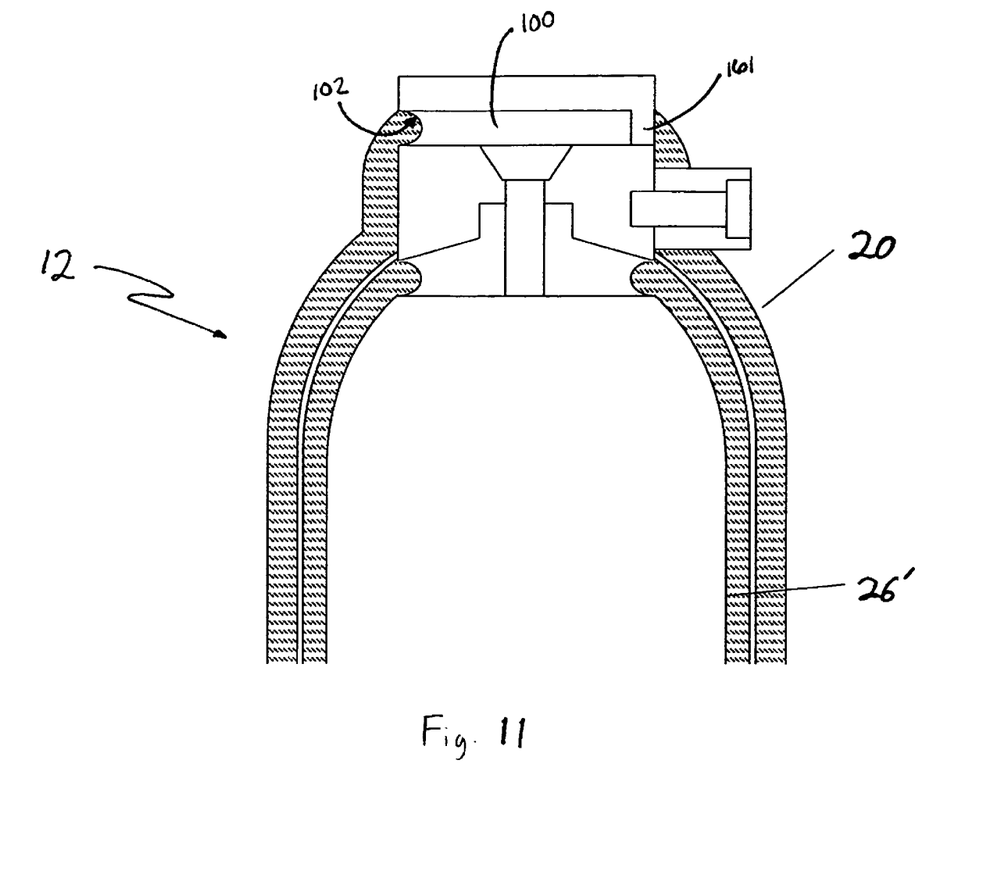
FIG. 11 shows an exemplary outer socket that has been formed around the exemplary inner socket and tooling.

As seen in FIG. 11, a dual socket 12 comprises an inner socket assembly 26, an outer socket assembly 20, and, as required by the nature of the specific dual socket system, apparatus to secure the inner socket to the residual limb, apparatus to secure the sockets to each other, and apparatus to secure the prosthetic limb to the outer socket. Such apparatus can be implemented in the manner described above.

Figure 8:
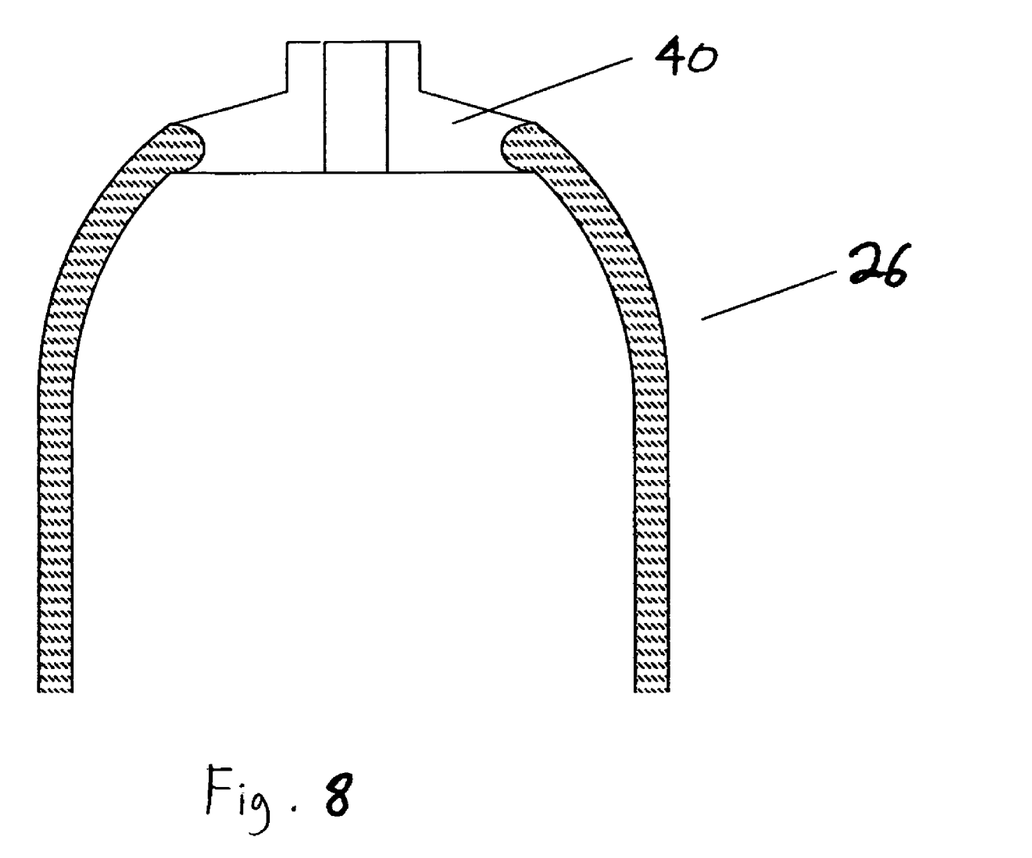
FIG. 8 shows an exemplary inner socket assembly.

Referencing FIG. 8, an exemplary methodology of the present invention starts by providing an inner socket assembly 26' comprising the inner socket and any requisite mounting apparatus, such as plate 40, incorporated therein. In the present exemplary embodiment, the mounting apparatus will vary depending on the particular dual socket system used. Referencing FIGS. 9 and 10, exemplary tooling components 152, 154, 156, 158, and 160 are provided. These tooling blocks are prefabricated and standardized for a given mounting system. Therefore, the tooling blocks can be mass-produced. Potentially, they could be sold as a kit along with the mounting system. In addition to a tooling apparatus standardized for a given mounting system, it is also possible to create universal tooling for use with multiple mounting systems.

Figure 9:
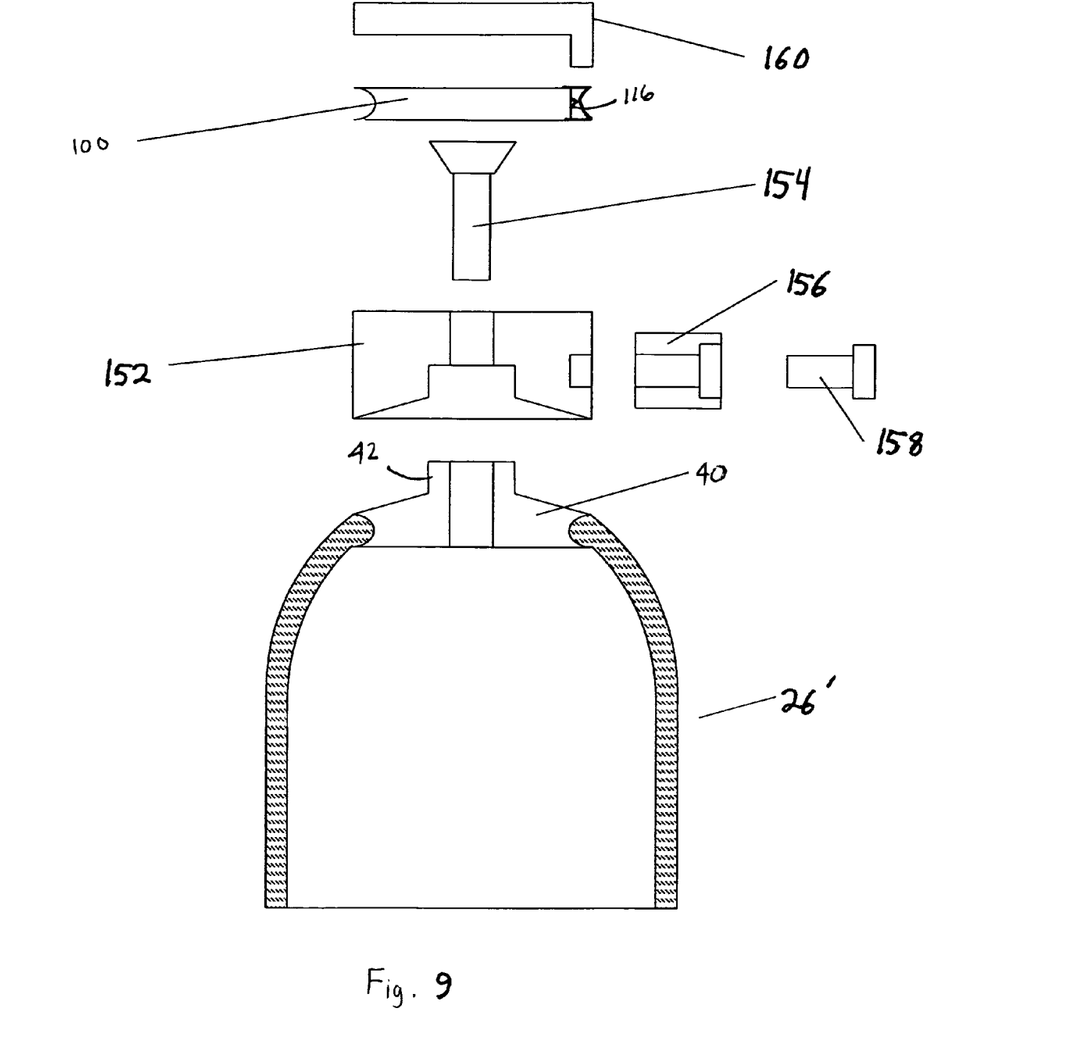
FIG. 9 shows an exploded view of another exemplary inner socket and exemplary prefabricated tooling blocks.
Figure 10:
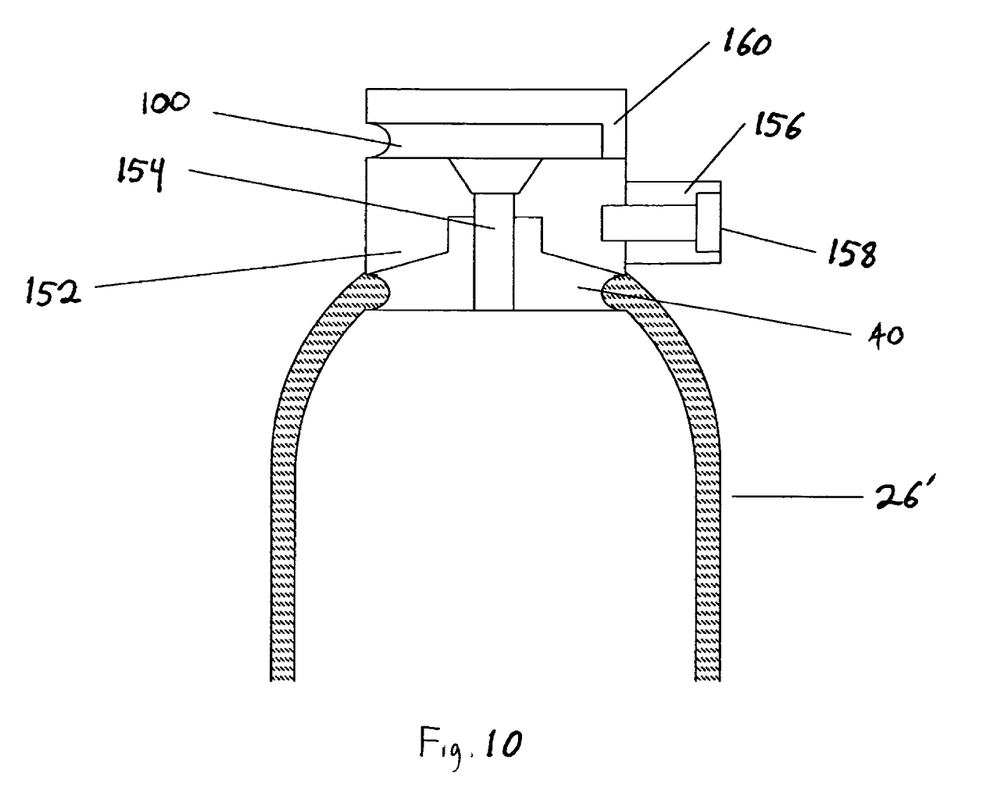
FIG. 10 shows the exemplary tooling and inner socket assembled and prepared for fabrication of the outer socket.

Referencing FIG. 9, the prefabricated tooling components 152, 154, 156, 158, and 160 are mounted on the distal end of the inner socket assembly 26', which includes the inner socket plate 40, but without the plunger pin 30 threaded thereto. First, a primary forming block (a positive mold end-block) 152 is secured to the distal end of the inner socket plate 40, using threaded fastener 154 (such as a bolt) threaded into the threaded interior of the attachment hub 42. The primary forming block 152 will create the primary void space between the two sockets for the shuttle lock 50 (or other associated components to be positioned between the distal ends of the two finished inner and outer sockets) during fabrication and ensures proper alignment of the inner and outer sockets. Next, a suspension sleeve (sacrificial, preferably) (not shown) is rolled over the inner socket 26' to provide a void for the roll-on sleeve used in the final product between the inner and outer sockets. Next, a PVA bag (not shown) or some other thin separating material is placed over the inner socket 26' and forming block 152 to keep the resin of the outer socket from such components during molding of the outer socket. A side porthole spacer 156 is then attached to the side of the primary forming block 152, using a threaded fastener 158. The side porthole spacer 156 allows for an opening to be created in the side of the outer socket 20, shown in FIG. 11, for the push button 51 of the shuttle lock 50. If needed, side porthole spacers of a different shape or size as well as a plurality of side porthole spacers could be used. Next, a circular base-plate, which is the attachment plate 100 in the present embodiment, is mounted on top of the primary forming block. In this embodiment, the attachment plate 100 will become a part of the outer socket in the completed assembly. Then, an outer spacer 160 is mounted on top of the outer socket plate 162. In the exemplary embodiment, the outer spacer 160 serves to cover the attachment plate 100 and protect it from accidental damage or clogging during formation of the outer socket. Finally, as shown in FIG. 11, the outer socket 20 is laminated around the tooling components and the inner socket assembly 26 using standard layer(s) of fabric like material and resin, or the outer socket is formed using any other means of socket fabrication presently known in the art or subsequently discovered. The attachment plate 100 is molded to the outer socket 20 during fabrication by filling lamination material within the circumferential indentation 102 during the lamination process, creating a mechanical coupling. Further the outer spacer 160 includes a proximally extending projection 161, that is inserted into a cutout 163 (See FIG. 6) in the distal end of the plate 100 adjacent to the vacuum port 116, so as to cover the vacuum port and prevent the vacuum port 116 and an adjacent area from being covered by outer socket material. This leaves an opening 165 (See FIG. 3) in the outer socket material being formed thereover so that the vacuum port 116 is accessible. Finally, after the outer socket material is sufficiently solidified/cured, the tooling (152, 154, 156, 158 and 160) is removed and the sockets are prepared for use as described above.

The methods enabled above are not intended to be limiting. Other methods are also possible. The specific tooling system(s) described above are not requisite for the invention. A method using as few as one tooling block or as many tooling blocks as are needed to form a complex geometry are within the scope of the invention.

Following from the above description and invention summaries, it should be apparent to persons of ordinary skill in the art that, while the methods and apparatuses herein described constitute exemplary embodiments of the present invention, it is to be understood that the inventions contained herein are not limited to the above precise embodiments and that changes may be made without departing from the scope of the invention as defined by the claims. Likewise, it is to be understood that the invention is defined by the claims and it is not necessary to meet any or all of the identified advantages or objects of the invention disclosed herein in order to fall within the scope of the claims, since inherent and/or unforeseen advantages of the present invention may exist even though they may not have been explicitly discussed herein.

What is claimed is:

1. A double-wall prosthetic limb socket assembly comprising:
   a first substantially rigid inner-wall socket adapted to receive a patient's residual limb; and
   a second substantially rigid outer-wall socket slidingly and removably seating the first inner-wall socket therein with a resilient liner fitted over the first substantially rigid inner wall socket and interposing the first substantially rigid inner-wall socket and the second substantially rigid outer-wall socket, the second outer-wall socket including,
   a distal, circular base-plate; and
   a molded circumferential wall bonded to and extending proximally from the distal, circular base-plate;
   the circular base-plate including a vacuum port extending radially from a circumferential outer side of the base-plate in fluid communication with a vacuum channel extending through the circular base-plate and out through an outlet hole in a proximal side of the circular base-plate;
   whereby, when the vacuum port is coupled to a vacuum pump, the vacuum will help to draw the first inner-wall socket into the second outer-wall socket;
   wherein the first substantially rigid inner-wall socket and the second substantially rigid outer-wall socket comprise at least one of (a) substantially hard thermoset plastic and (b) layers of fabric-type material impregnated with cured resin; wherein the resilient liner comprises a substantially closed distal end and an open proximal end; and wherein the resilient liner is adapted to be rolled proximally over the first substantially rigid inner wall socket.

2. The double-wall prosthetic limb socket assembly of claim 1, wherein the circular base-plate includes one or more indentations extending into a circumferential outer side of the circular base-plate into which material of the molded circumferential wall is received, thus facilitating a mechanical bond between the circular base-plate and the molded circumferential wall.

3. The double-wall prosthetic limb socket assembly of claim 1, wherein the circular base-plate is less than 0.75 inches thick.

4. The double-wall prosthetic limb socket assembly of claim 1, further comprising:
   a first one of a female and a male component of a mechanical lock seated between the first inner-wall socket and the second outer-wall socket over a proximal end of the circular base-plate; and
   a complimentary component of the first component of the mechanical lock extending distally from the first inner-wall socket and mating with the first component of the mechanical lock thus providing a mechanical lock between the first inner-wall socket and second outer-wall socket.

5. The double-wall prosthetic limb socket assembly of claim 4, wherein:
   the first component of the mechanical lock is a male, ratchet-type interlock pin; and
   the complimentary component of the mechanical lock is a female, biased-pawl type lock base.

6. The double-wall prosthetic limb socket assembly of claim 5, wherein the interlock pin extends from the resilient liner fitted over the first inner-wall socket and includes a vacuum channel extending completely therethrough in fluid communication with the outlet hole of the circular base-plate when locked into the lock base and providing a vacuum between the resilient sleeve and the inner-wall socket.

7. The double-wall prosthetic limb socket assembly of claim 1, wherein the distal end of the circular base-plate includes a fastener for coupling to a prosthetic limb upright assembly.

8. The double-wall prosthetic limb socket assembly of claim 1, wherein the distal end of the circular base-plate is coupled to a prosthetic limb pyramid coupling component.

9. The double-wall prosthetic limb socket assembly of claim 1, wherein the substantially hard thermoset plastic comprises substantially hard polyester resin, acrylic resin, polypropylene, and polyethylene.

10. A double-wall prosthetic limb socket assembly comprising:
    a first substantially rigid inner-wall socket adapted to receive a patient's residual limb;
    a second substantially rigid outer-wall socket slidingly and removably seating the first inner-wall socket therein with a resilient liner fitted over the first substantially rigid inner wall socket and interposing the first substantially rigid inner-wall socket and the second substantially rigid outer-wall socket, the second outer-wall socket including,
    a distal, circular base-plate; and
    a molded circumferential wall bonded to and extending proximally from the distal, circular base-plate;
    a first one of a female and a male component of a mechanical lock seated between the first inner-wall socket and the second outer-wall socket over a proximal end of the circular base-plate; and
    a complimentary component of the first component of the mechanical lock extending distally from the first inner-wall socket and mating with the first component of the mechanical lock thus providing a mechanical lock between the first inner-wall socket and second outer-wall socket;
    the circular base-plate including a vacuum port extending through an outer surface of the base-plate in fluid communication with a vacuum channel extending through the circular base-plate and an outlet hole in a proximal side of the circular base-plate;
    whereby, when the vacuum port is coupled to a vacuum pump, the vacuum will help to draw the first inner-wall socket into the second outer-wall socket;
    wherein the first substantially rigid inner-wall socket and the second substantially rigid outer-wall socket comprise at least one of (a) substantially hard thermoset plastic and (b) layers of fabric-type material impregnated with cured resin; wherein the resilient liner comprises a substantially closed distal end and an open proximal end; and wherein the resilient liner is adapted to be rolled proximally over the first substantially rigid inner wall socket.

11. The double-wall prosthetic limb socket assembly of claim 10, wherein:
the first component of the mechanical lock is a male, ratchet-type interlock pin; and
the complimentary component of the mechanical lock is a female, biased-pawl type lock base.

12. The double-wall prosthetic limb socket assembly of claim 11, wherein the interlock pin extends from the resilient liner fitted over the first inner-wall socket and includes a vacuum channel extending completely therethrough in fluid communication with the outlet hole of the circular base-plate when locked into the lock base and providing a vacuum between the resilient sleeve and the inner-wall socket.

13. The double-wall prosthetic limb socket assembly of claim 10, wherein the distal end of the circular base-plate includes a fastener for coupling to a prosthetic limb upright assembly.

14. The double-wall prosthetic limb socket assembly of claim 10, wherein the distal end of the circular base is coupled to a prosthetic limb pyramid coupling component.

15. The double-wall prosthetic limb socket assembly of claim 10, wherein the substantially hard thermoset plastic comprises substantially hard polyester resin, acrylic resin, polypropylene, and polyethylene.

16. A double-wall prosthetic limb socket assembly comprising:
a first substantially rigid inner-wall socket adapted to receive a patient's residual limb; and
a second substantially rigid outer-wall socket slidingly and removably seating the first inner-wall socket therein with a resilient liner fitted over the first inner wall socket and interposing the first inner-wall socket and the second outer-wall socket, the second outer-wall socket including,
a distal, circular base-plate; and
a molded circumferential wall bonded to and extending proximally from the distal, circular base-plate;
the circular base-plate including one or more indentations extending into a circumferential outer side of the circular base-plate into which material of the molded circumferential wall is received, thus facilitating a mechanical bond between the circular base-plate and the molded circumferential wall;
the circular base-plate also including a vacuum port extending through an outer surface of the base-plate in fluid communication with a vacuum channel extending through the circular base-plate and an outlet hole in a proximal side of the circular base-plate;
whereby, when the vacuum port is coupled to a vacuum pump, the vacuum will help to draw the first inner-wall socket into the second outer-wall socket;
wherein the first substantially rigid inner-wall socket and the second substantially rigid outer-wall socket comprise at least one of (a) substantially hard thermoset plastic and (b) layers of fabric-type material impregnated with cured resin; wherein the resilient liner comprises a substantially closed distal end and an open proximal end; and wherein the resilient liner is adapted to be rolled proximally over the first substantially rigid inner wall socket.

17. The double-wall prosthetic limb socket assembly of claim 15, wherein the circular base-plate is less than 0.75 inches thick.

18. A double-wall prosthetic limb socket assembly comprising:
a first substantially rigid inner-wall socket adapted to receive a patient's residual limb; and
a second substantially rigid outer-wall socket slidingly and removably seating the first inner-wall socket therein with a resilient liner fitted over the first substantially rigid inner wall socket and interposing the first substantially rigid inner-wall socket and the second substantially rigid outer-wall socket, the second outer-wall socket including,
a distal, circular base-plate; and
a molded circumferential wall bonded to and extending proximally from the distal, circular base-plate;
the circular base-plate including one or more projections extending from a circumferential outer side of the circular base-plate around which material of the molded circumferential wall is received, thus facilitating a mechanical bond between the circular base-plate and the molded circumferential wall;
the circular base-plate also including a vacuum port extending through an outer surface of the base-plate in fluid communication with a vacuum channel extending through the circular base-plate and an outlet hole in a proximal side of the circular base-plate;
whereby, when the vacuum port is coupled to a vacuum pump, the vacuum will help to draw the first inner-wall socket into the second outer-wall socket;
wherein the first substantially rigid inner-wall socket and the second substantially rigid outer-wall socket comprise at least one of (a) substantially hard thermoset plastic and (b) layers of fabric-type material impregnated with cured with resin; wherein the resilient liner comprises a substantially closed distal end and an open proximal end; and wherein the resilient liner is adapted to be rolled proximally over the first substantially rigid inner wall socket.

\* \* \* \* \*